United States Patent [19]

Paige

[11] Patent Number: 5,255,527
[45] Date of Patent: Oct. 26, 1993

[54] METHOD OF TESTING THE PURITY OF REFRIGERANT FLOWING THROUGH A REFRIGERATION SYSTEM

[75] Inventor: Lowell E. Paige, Pennellville, N.Y.

[73] Assignee: Carrier Corporation, Syracuse, N.Y.

[21] Appl. No.: 815,775

[22] Filed: Jan. 2, 1992

[51] Int. Cl.⁵ .......................................... F25B 43/00
[52] U.S. Cl. ........................................ 62/85; 62/129; 62/149
[58] Field of Search ................... 62/149, 174, 195, 85, 62/125, 126, 127, 129

[56] References Cited

U.S. PATENT DOCUMENTS

| | | | |
|---|---|---|---|
| 4,316,364 | 2/1982 | Spauschus | 62/85 X |
| 4,649,711 | 3/1987 | Sibley et al. | 62/129 |
| 4,803,843 | 2/1989 | Otto | 62/85 |
| 4,866,994 | 9/1989 | Baker | 62/125 X |
| 4,923,806 | 5/1990 | Klodowski | 62/128 X |

Primary Examiner—Harry B. Tanner

[57] ABSTRACT

A refrigeration system having a refrigerant compressor which has a refrigerant purity sampling circuit in parallel fluid flow communication therewith. The purity sampling circuit includes a refrigerant purity tube holder in which a refrigerant purity tube may be removably supported to thereby cause a flow of refrigerant therethrough during a purity sampling test due to the pressure differential across the compressor. The refrigerant purity sampling holder is adapted to receive an empty open ended test tube therein. The empty tube is left in the holder at all times, except when it is desired to perform a purity sampling test, in which case the empty open tube is removed and an active purity sampling tube is inserted therein. The system is further provided with the capability of purging the empty open ended tube and the refrigerant purity sampling circuit prior to the installation of an active tube.

3 Claims, 9 Drawing Sheets

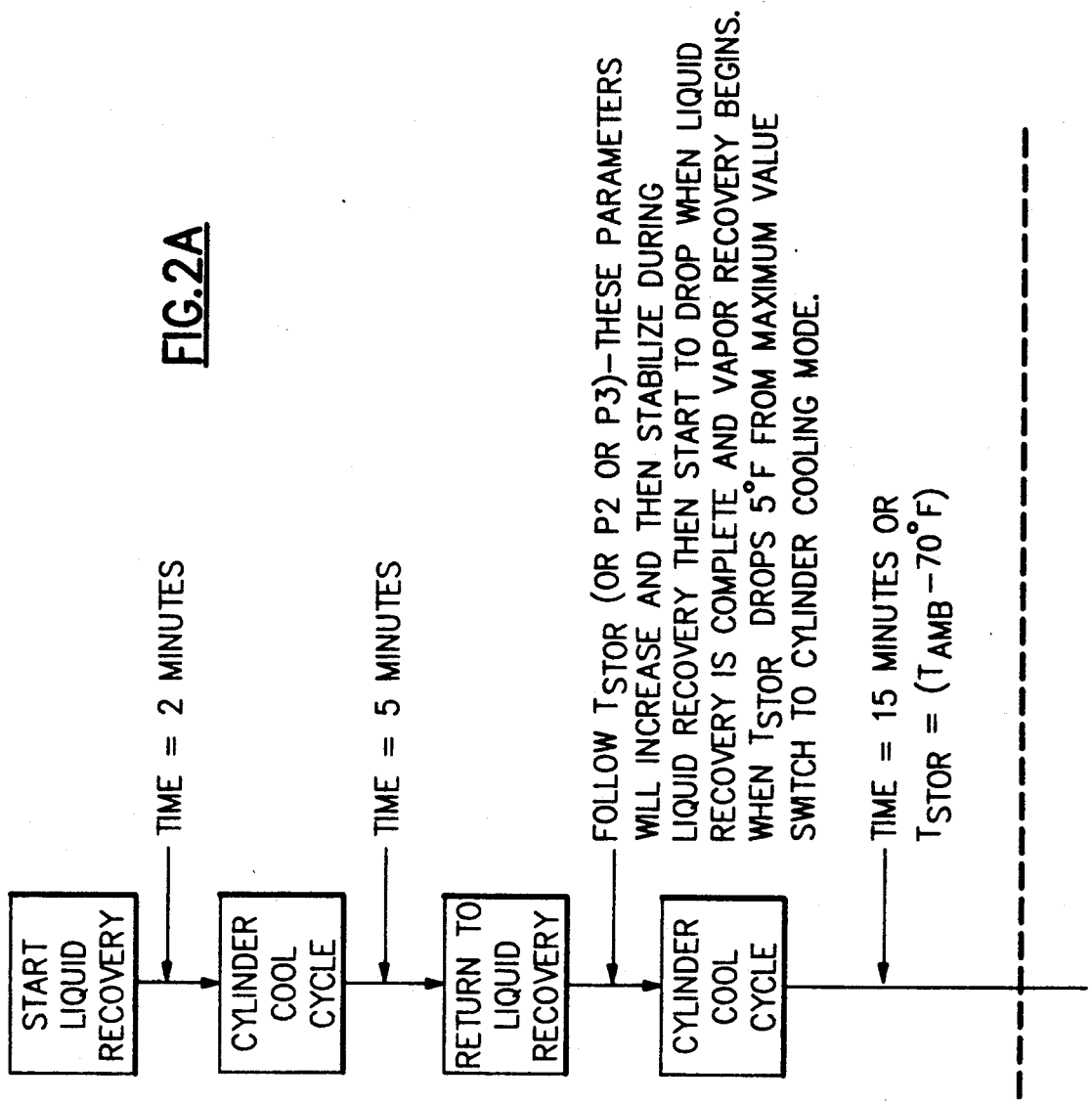

VAPOR RECOVERY MODE
LOGIC DIAGRAM

REFRIGERANT RECOVERY/RECYCLE
UNIT COMPONENT/MODE CHART

| MODE | COMPONENT | | | | | | |
|---|---|---|---|---|---|---|---|
| | SV1 | SV2 | SV3 | SV4 | SV5/SV6 | SV7 | COMPRESSOR/COND FAN |
| STANDBY | CL | CL | CL | CL | CL | CL | OFF |
| SERVICE | OP | OP | OP | OP | CL | OP | OFF |
| RECOVERY (LIQUID) | OP | CL | CL | CL | CL | OP | ON |
| RECOVERY (VAPOR) | CL | CL | OP | OP | CL | CL | ON |
| CYLINDER COOL | OP | CL | CL | CL | CL | CL | ON |
| RECYCLE | OP | CL | CL | OP | CL | CL | ON |
| TOTALEST | OP | OP | CL | OP | OP | CL | ON |
| RECHARGE | CL | CL | CL | CL | CL | OP | OFF |

NOTES: SOLENOID VALVES SV5 AND SV6 OPERATE TOGETHER AS A SINGLE OUTPUT FROM MICROPROCESSOR.

COMPRESSOR MOTOR/COND FAN MOTOR OPERATE TOGETHER AS A SINGLE OUTPUT FROM MICROPROCESSOR.

OP = OPEN (ENERGIZED)
CL = CLOSED (DE-ENERGIZED)
ON = ENERGIZED
OFF = DE-ENERGIZED

FIG.7

METHOD OF TESTING THE PURITY OF REFRIGERANT FLOWING THROUGH A REFRIGERATION SYSTEM

BACKGROUND OF THE INVENTION

1. Field of the Invention

This invention relates to refrigerant recovery and purification systems. More specifically it relates to an arrangement for testing the purity of the refrigerant which has been recovered and purified by such a system.

2. Description of The Prior Art

A wide variety of mechanical refrigeration systems are currently in use in a wide variety of applications. These applications include domestic refrigeration, commercial refrigeration, air conditioning, dehumidifying, food freezing, cooling and manufacturing processes, and numerous other applications. The vast majority of mechanical refrigeration systems operate according to similar, well known principals, employing a closed-loop fluid circuit through which a refrigerant flows. A number of saturated fluorocarbon compounds and azeotropes are commonly used as refrigerants in refrigeration systems. Representative of these refrigerants are R-12, R-22, R-500 and R-502.

Those familiar with mechanical refrigeration systems will recognize that such systems periodically require service. Such service may include removal, of, and replacement or repair of, a component of the system. Further during normal system operation the refrigerant can become contaminated by foreign matter within the refrigeration circuit, or by excess moisture in the system. The presence of excess moisture can cause ice formation in the expansion valves and capillary tubes, corrosion of metal, copper plating and chemical damage to insulation in hermetic compressors. Acid can be present due to motor burn out which causes overheating of the refrigerant. Such burn outs can be temporary or localized in nature as in the case of a friction producing chip which produces a local hot spot which overheats the refrigerant. The main acid of concern is HCL but other acids and contaminants can be produced as the decomposition products of oil, insulation, varnish, gaskets and adhesives. Such contamination may lead to component failure or it may be desirable to change the refrigerant to improve the operating efficiency of the system.

When servicing a refrigeration system it has been the practice for the refrigerant to be vented into the atmosphere, before the apparatus is serviced and repaired. The circuit is then evacuated by a vacuum pump, which vents additional refrigerant to the atmosphere, and recharged with new refrigerant. This procedure has now become unacceptable for environmental reasons, specifically, it is believed that the release of such fluorocarbons depletes the concentration of ozone in the atmosphere. This depletion of the ozone layer is believed to adversely impact the environment and human health. Further, the cost of refrigerant is now becoming an important factor with respect to service cost, and such a waste of refrigerant, which could be recovered, purified and reused, is no longer acceptable.

To avoid release of fluorocarbons into the atmosphere, devices have been provided that are designed to recover the refrigerant from refrigeration systems. The devices often include means for processing the refrigerants so recovered so that the refrigerant may be reused. Representative examples of such devices are shown in the following U.S. Pat. Nos.: 4,441,330 "Refrigerant Recovery And Recharging System" to Lower et al; 4,476,688 "Refrigerant Recovery And Purification System" to Goddard; 4,766,733 "Refrigerant Reclamation And Charging Unit" to Scuderi; 4,809,520 "Refrigerant Recovery And Purification System" to Manz et al; 4,862,699 "Method And Apparatus For Recovering, Purifying and Separating Refrigerant From Its Lubricant" to Lounis; 4,903,499 "Refrigerant Recovery System" to Merritt; and 4,942,741 "Refrigerant Recovery Device" to Hancock et al.

Following the operation of such systems to recover and purify refrigerant, it is desirable, before reusing the refrigerant, to test the purity of that refrigerant. At best, existing systems are provided with sight glasses which may give some indication of the present of moisture in the recovered refrigerant.

U.S. Pat. No. 4,923,806 entitled "Method and Apparatus for Refrigerant Testing In A Closed System" is assigned to the assignee of the present invention and is directed to a method and apparatus for detecting contaminants in a refrigerant medium. This patent teaches the use of single use transparent glass testing tubes which are sealed until used and which contain therein an oil removal section, a water removal and indicating section, and, an acid indicating section. In use, the ends of the glass testing tubes are broken off and the tube is placed in a tube holder apparatus which functions to seal the tube so that all of the refrigerant flows directed through the tube. The presence of contaminants is indicated by a color change which may be quantified by comparison to a color chart and/or the extent of the promulgation of the color change in the indicating media. The refrigerant sample is allowed to pass through the testing tube and then to the atmosphere. The venting of refrigerant gas to the atmosphere is not considered to be environmentally acceptable expedient.

A commonly assigned U.S. patent application, Ser. No. 612,641, filed on Nov. 13, 1990, discloses a system for sampling the purity of refrigerant flowing through a refrigeration circuit. This system makes use of the system of U.S. Pat. No. 4,923,806, described above. The system described in the above identified patent application is shown as applied to a refrigerant recovery and purification system. In that system the operator had two options with respect to the refrigerant purity sampling feature. The first option was not to select this mode of operation, in which case the sampling tube fixture may or may not contain a refrigerant quality testing tube. Accordingly, the fixture could be open to the atmosphere. The second option was to select the refrigerant purity sampling feature. In that case, the user was instructed to install a purity test tube into the fixture prior to the recovery/recycle operation, and, the unit was programmed to automatically perform the purity test at the end of the cycle selected.

It has been found that, particularly with more sensitive sampling tubes, moisture in the surrounding air, moisture in the tube holder, and/or moisture from previous refrigerant samples, has adversely affected the accuracy and repeatability of moisture level reading in this system.

SUMMARY OF THE INVENTION

It is an object of the present invention to provide a refrigerant purity test system for a refrigeration system which minimizes the effects of external moisture on the results of the purity test.

It is a further object of the present invention to incorporate a refrigerant purity test system into a refrigerant recovery and purification system in a manner which assures that the refrigerant tested by a purity test system is representative of the refrigerant circulating in the recovery system.

These and other objects of the invention are achieved in a refrigeration system having a refrigerant compressor which has a refrigerant purity sampling circuit in parallel fluid flow communication therewith. The purity sampling circuit includes a refrigerant purity tube holder in which a refrigerant purity tube may be removably supported to thereby cause a flow of refrigerant therethrough during a purity sampling test due to the pressure differential across the compressor. The refrigerant purity sampling holder is adapted to receive an empty open ended test tube therein. The empty tube is left in the holder at all times, except when it is desired to perform a purity sampling test, in which case the empty open tube is removed and an active purity sampling tube is inserted therein. The system is further provided with the capability of purging the empty open ended tube and the refrigerant purity sampling circuit prior to the installation of an active tube.

BRIEF DESCRIPTION OF THE DRAWINGS

The novel features that are considered characteristic of the invention are set forth with particularity in the appended claims. The invention itself, however, both as to its organization and its method of operation, together with additional objects and advantages thereof, will be best understood from the following description of the preferred embodiment when read in connection with the accompanying drawings wherein;

FIG. 2A is a flow chart of an exemplary program for controlling the system in a liquid recovery mode of operation;

FIG. 7 is a chart showing the operation of the various components of the system during different modes of operation;

DESCRIPTION OF THE PREFERRED EMBODIMENT

Figure 1:
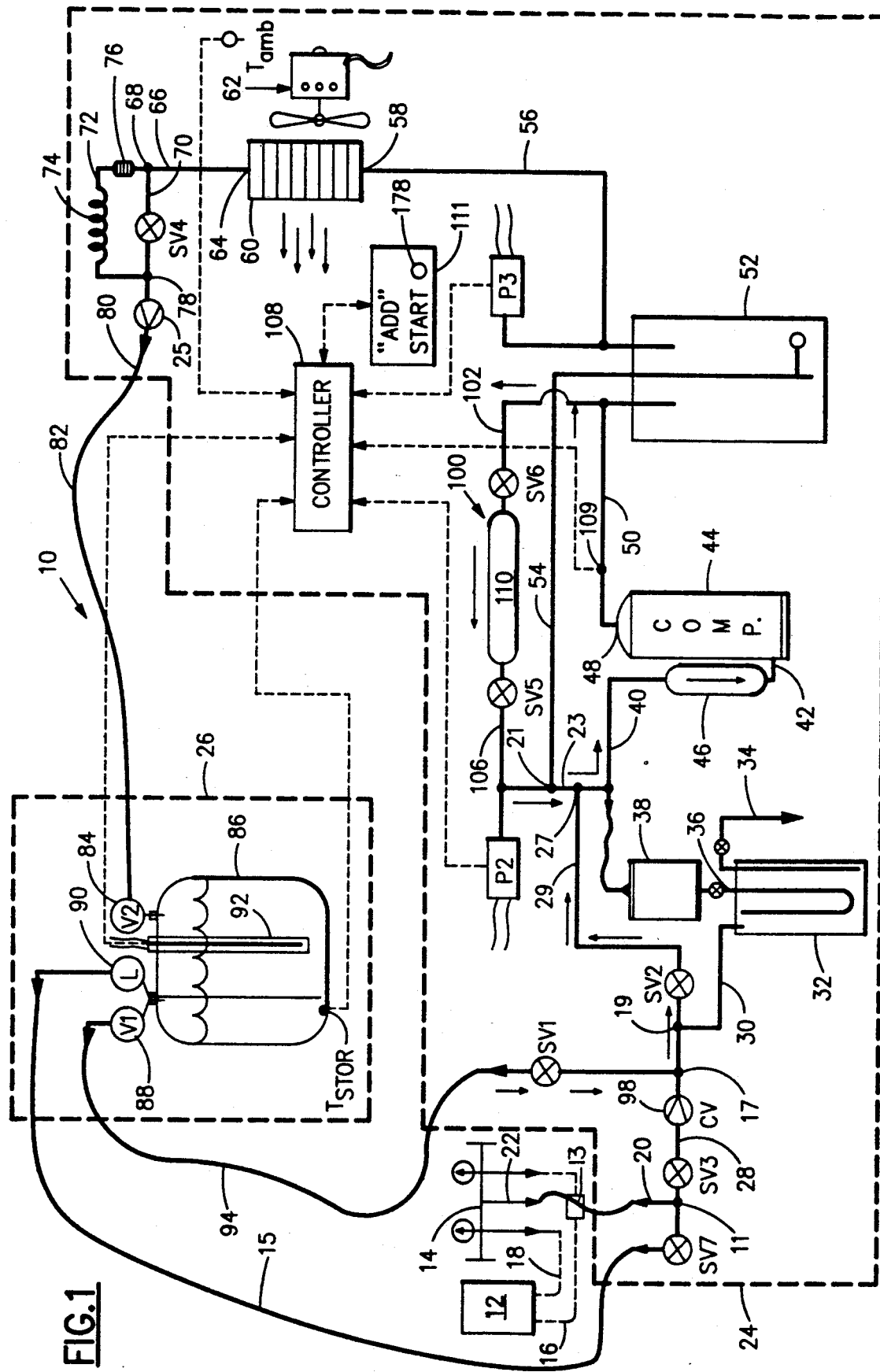
FIG. 1 is a diagrammatical representation of a refrigeration recovery and purifying system embodying the principles of the present invention.

An apparatus for recovering and purifying the refrigerant contained in a refrigeration system is generally shown at reference numeral 10 in FIG. 1. The refrigeration system to be evacuated is generally indicated at 12 and may be virtually any mechanical refrigeration system.

As shown the interface or tap between the recovery and purification system 10 and the system being serviced 12 is a standard gauge and service manifold 14. The manifold 14 is connected to the refrigeration system to be serviced in a standard manner with one line 16 connected to the low pressure side of the system 12 and another line 18 connected to the high pressure side of the system. A high pressure refrigerant line 20 is interconnected between the service connection 22 of the service manifold and a T connection 11 for coupling the line 20 to the recovery system 10.

Located in the interconnecting line 20 is a filter-dryer 13 which is mounted external of the recovery system. This device as will be seen, is normally installed in the line 20 only when the system is to be operated first in the liquid recovery mode of operation.

The recovery system 10 includes two sections, as shown in FIG. 1 the components and controls of the recovery system are contained within a self contained compact housing (not shown) schematically represented by the dotted line 24. A refrigerant storage section of the system is contained within the confines of the dotted lines 26. The details of each of these sections and their interconnection and interaction with one another will now be described in detail.

As will be appreciated as the description of the operation of the system continues there are two refrigerant paths extending from the T-connection 11 at the end of interconnecting line 20. The first path, i.e. the liquid path, extends to the left of the T-11 to an electrically actuatable solenoid valve SV7. This valve will selectively allow refrigerant to pass therethrough when actuated to its open position or will prevent the flow of refrigerant therethrough when electrically actuated to its closed position. Additional electrically actutatable solenoid valves contained in the system operate in the same conventional manner. From SV7 a liquid refrigerant line 15 extends to the refrigerant storage section of the system 26 where it communicates through a valve 90 with a refrigerant storage cylinder 86. In the liquid recovery mode of operation of the system liquid refrigerant passes through the line 15 directly from the refrigeration system 12 to the storage cylinder 86.

When the system is operated in the vapor recovery mode gaseous refrigerant flowing through the interconnecting line 20 flows through the T-11 and to the right to electrically actuatable solenoid valve SV3. From SV3 refrigerant flows via conduit 28, through a check valve 98 and a T-connection 17 to another T-connection 19. From the T-19 a conduit 30 conducts the refrigerant to the inlet of a combination accumulator/oil trap 32 having a drain valve 34. Refrigerant gas is then drawn from the oil trap through conduit 36 to an acid purification filter-dryer 38 where impurities such as acid, moisture, foreign particles and the like are removed before the gases are passed via conduit 40 to the suction port 42 of the compressor 44. A suction line accumulator 46 is disposed in the conduit 42 to assure that no liquid refrigerant passes to the suction port 42 of the compressor. The compressor 44 is preferably of the rotary type, which are readily commercially available from a number of compressor manufacturers but may be of any type such as reciprocating, scroll or screw.

From the compressor discharge port 48 gaseous refrigerant is directed through conduit 50 to a conventional float operated oil separator 52 where oil from the recovery system compressor 44 is separated from the gaseous refrigerant and directed via float controlled return line 54 to a T-connection 21. From the T-21, the oil passes via conduit 23 to the conduit 40 which communicates with the suction port of the compressor. From the outlet of the oil separator 52 gaseous refrigerant passes via conduit 56 to the inlet 58 of a heat exchanger/condenser coil 60. An electrically actuated condenser fan 62 is associated with the coil 60 to direct the flow of ambient air through the coil as will be described in connection with the operation of the system.

From the outlet 64 of the condenser coil 60 an appropriate conduit 66 conducts refrigerant to a T-connection 68. From the T 68 one conduit 70 passes to another electrically actuated solenoid valve SV4 while the other branch 72 of the T passes to a suitable refrigerant expansion device 74. In the illustrated embodiment the expansion device 74 is a capillary tube and a strainer 76 is disposed in the refrigerant line 72 upstream from the capillary tube to remove any particles which might potentially block the capillary. It should be appreciated that the expansion device could comprise any of the other numerous well known refrigerant expansion devices which are widely commercially available. The conduit 72 containing the expansion device 74 and the conduit 70 containing the valve SV4 rejoin at a another T connection 78 downstream from both devices. It will be appreciated that the solenoid valve SV4 and the expansion device 74 are in a parallel fluid flow relationship. As a result, when the solenoid valve SV4 is open the flow of refrigerant will be, because of the high resistance of the expansion device, through the solenoid valve in a substantially unrestricted manner. On the other hand, when the valve SV4 is closed, the flow of refrigerant will be through the high resistance path provided by the expansion device. Combination devices such as electronically actuated expansion valves are known which would combine the functions of the valves SV4 and the capillary tube 74, however, as configured and described above, the desired function is obtained at a minimum cost.

From the T-78 a conduit 80 passes to an appropriate coupling (not shown) for connection of the system as defined by the confines of the line 24, via a flexible refrigerant line 82 to the inlet port 84 of the previously referred to refillable refrigerant storage container 86. The conduit 80 contains a check valve 25 which is adapted to allow flow only in the direction from the T-78 to the storage cylinder 86. The container 86 is of conventional construction and includes a second port 88 adapted for vapor outlet. The storage cylinder 86 further includes a liquid level indicator 92. The liquid level indicator, for example, may comprise a compact continuous liquid level sensor of the type available from Imo Delaval Inc., Gems Sensors Division. Such an indicator is capable of providing an electrical signal indicative of the level of the refrigerant contained within the storage cylinder 86.

Refrigerant line 94 interconnects the vapor outlet 88 of the cylinder 86 with the T connection 76 in the conduit 28. An additional electrically actuated solenoid valve SV1 is located in the line 94.

With continued reference to FIG. 1 a refrigerant purity sampling circuit 100 is included in the system in a parallel fluid flow arrangement with the compressor 44. The purity sampling circuit 100 includes an inlet conduit 102 in fluid communication with the inlet conduit 50 of the oil separator 52. The inlet conduit 102 has an electrically actuated solenoid valve SV6 disposed there along and from there passes to the inlet of a sampling tube holder 110. The outlet of the sampling tube holder 104 is interconnected via conduit 106 with T-21, conduit 23, and with the conduit 40 which communicates with the suction port 42 of the compressor. An electrically controlled solenoid valve SV5 is disposed in the conduit 106.

The conduit section 23 is also provided with a T-connection 27. The T-27 is connected via a refrigerant sampling conduit 29 to the T-connection 19 in conduit 28. A normally closed solenoid actuated flow control valve SV2 is located in the conduit 29.

The solenoid valves SV5 and SV6, when closed, isolate the sampling tube holder 104 from the system and allow easy replacement of the sampling tube contained therein. The sampling tube holder is preferably of the type illustrated in FIGS. 9 and 10. Such a holder is described and claimed in commonly assigned U.S. patent application Ser. No. 612,639, filed on Nov. 13, 1990.

Figure 9:
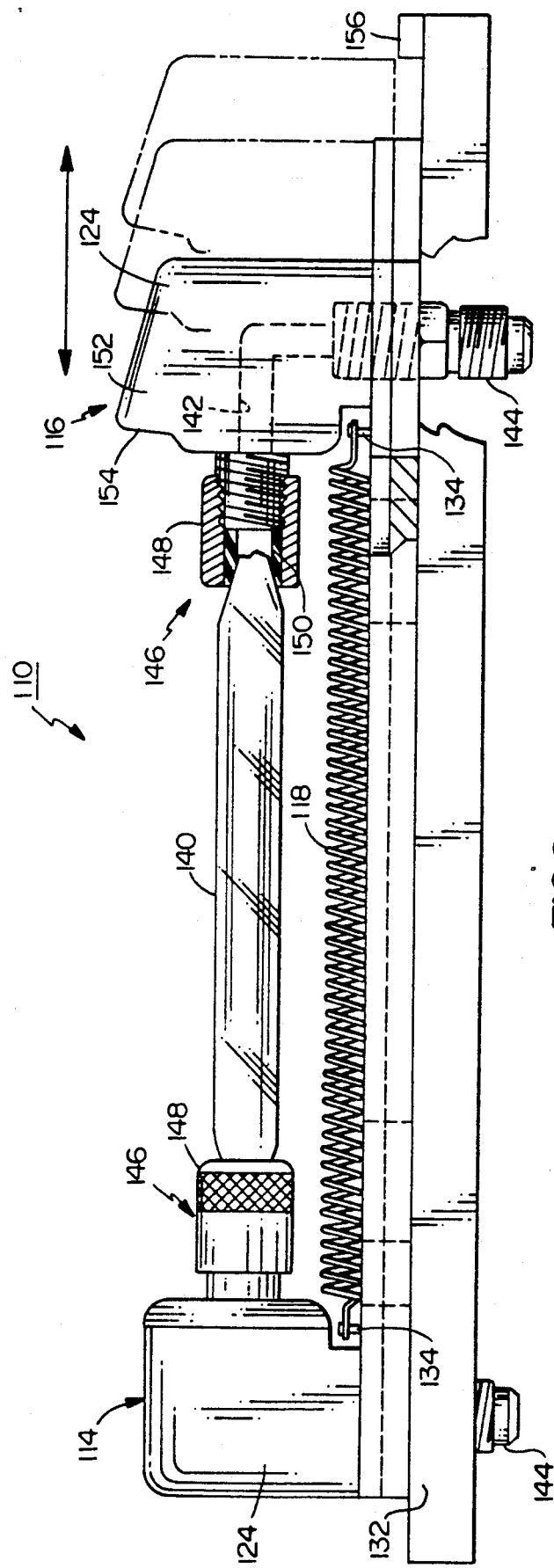
FIG. 9 is a side view of the sampling tube holder assembly used in connection with the method of the present invention.
Figure 10:
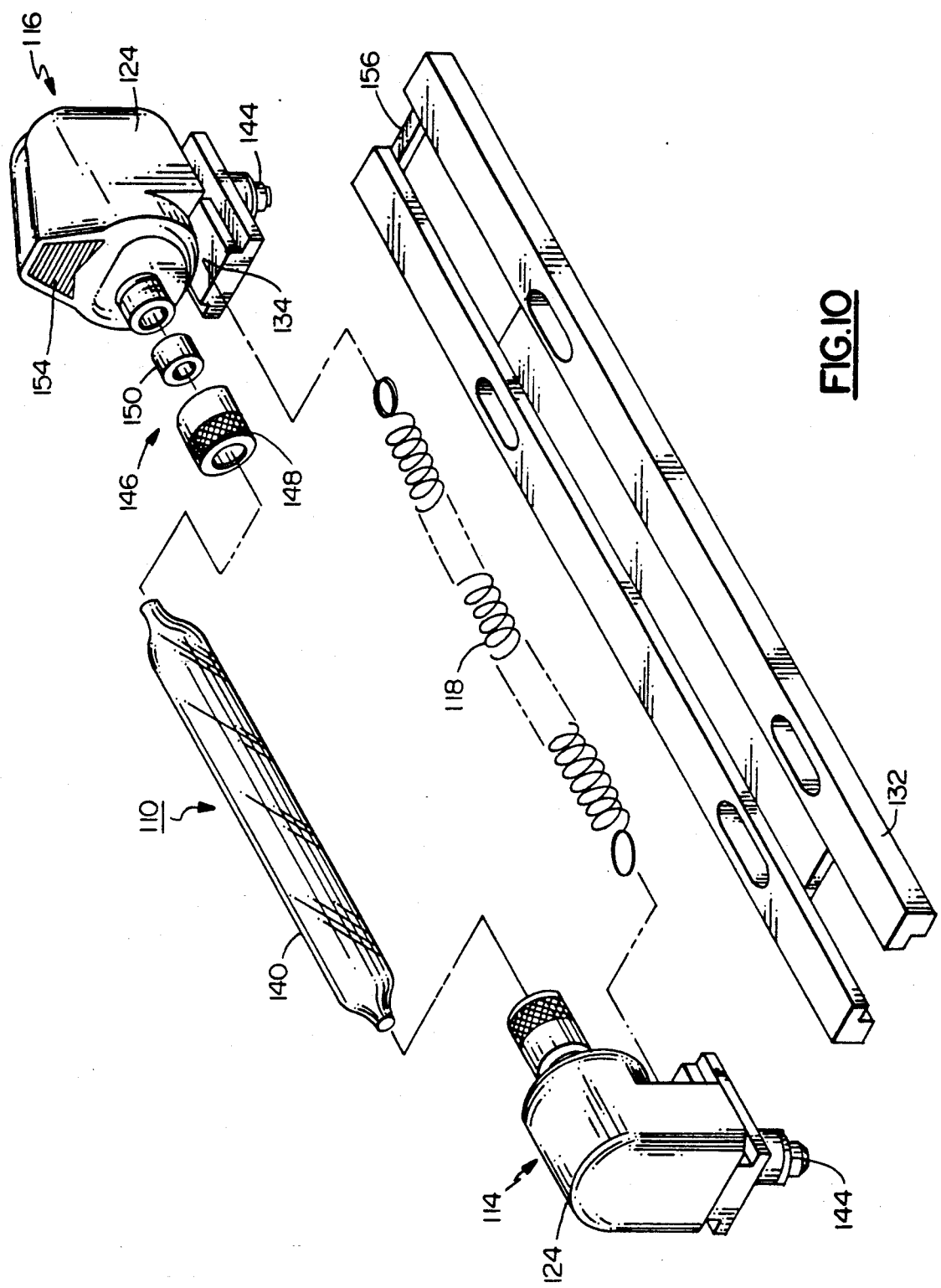
FIG. 10 is a perspective exploded view of the sampling tube holder assembly of FIG. 9.

Referring now to FIGS. 9 and 10 the sampling tube holder 110 the includes a supporting base 112, a fixed end fitting 114, a movable end fitting 116, and, an interconnecting biassing spring 118.

The structure of the base 112 takes on the appearance of a rail in that it comprises two parallel extending, inverted L shaped sections 120 which are interconnected by a central web like portion 122 which is shorter than the section 120. The base essentially defines an elongated H shape as viewed from the top with the legs being longer at the right hand end of the base upon which the moveable end fitting 116 is mounted. Four elongated mounting slots 124 are provided, two in each rail, to facilitate ease of mounting of the fixture.

The end fittings 114 and 116 are substantially identical each having a main body portion 124 and a mounting portion 126 which extends from the lower end of the body and defines an inverted T shaped cross section. The two laterally extending legs 128 of the mounting portion are adapted to be received in sliding relationship with mating channel like surfaces 130 defined by the inverted L shaped portions of the legs forming the ends of the base 112. The lower surface 132 of the main body portion rests on the top of the rails 120. The fixed end fitting 114 is appropriately fastened to the base 112 for example by a suitable adhesive.

The moveable end fitting 116 is slideably received in the end of the base 112 having the longer legs and as will be seen is moveable axially with respect to the base as depicted in FIG. 1. Each of the end fittings 114 and 116 is provided with a spring anchor device 134 mounted on the upper side of the T shaped mounting extension 126. The longitudinally extending tension spring 118 having suitable anchoring loops 138 at each end engages the anchor devices 134 of both the fixed and moveable end fittings. The length of the spring is such that when anchored to both end fittings 114, 116 as depicted in FIG. 1 a substantial force is exerted on the moveable end fitting to the left. This force is critical to obtaining and maintaining the seal between the fixture and the sampling tube 140 mounted therein as will be appreciated as the engagement of the end fittings 114 and 116 with the sampling tube is described.

Each of the end fittings 114 and 116 has a flow path defined therethrough which includes an internal channel 142 interconnected by a pair of threaded fittings. A first threaded flow fitting 144 is mounted to the mounting extension 126. In the illustrated embodiment each of the fittings 144 is provided with a standard ¼ inch flare fitting to facilitate attachment to appropriate flow conduits in a testing system.

A second set of fittings 146 which define the sampling tube support and seal configuration are mounted in the bodies 124 of the end fittings 114 and 116 such that they are in confronting axially aligned relationship with one another when the device is assembled. Each of the fittings 146 defines a standard ¼ inch flare fitting upon which a ¼ inch flare cap 148 with a ¼ inch diameter hole drilled therein is threadably engaged. A cylindrical rubber seal 150 is disposed within each of the flare caps 148 as shown in the broken away view of the seal arrangement on the moveable end fitting 116 in FIG. 1.

The seal 150 is inserted into the flare cap 148, prior to assembly of the cap to flare fitting, through the opening adjacent to the threaded end. When the cap 148 is threaded into the fitting the seal is retained between the fitting and an annular lip 151 formed at the end of the flare cap 148.

As thus described a sample tube 140 is installed within the fixture 110 by first breaking off ends of the glass sample tube, pulling back the moveable end fitting 116 an appropriate distance to allow one end of the sampling tube to be inserted into engagement with the seal fitting 146 of the fixed end fitting 114, and, while holding the tube in proper alignment, allowing the moveable fixture 116 to move, under the force of the spring, into appropriate sealing engagement with the other end of the sampling tube. As thus installed the flare fittings and the seal elements 150 inside the flare cap 148, in combination with the constant tension provided by the spring, establish a leak proof path through the fixture.

In the preferred embodiment the spring is selected to maintain a constant five pounds of tension against the seals 150 which will allow a pressure maximum of over 200 psi before leakage occurs around the seal. It should be appreciated that the rubber seals may, with continued use, lose there sealing integrity as they are subject to damage by the rough ends of the sampling tube 140. The seals 150 may be readily removed and replaced with new ones as the flare caps may be unscrewed by hand and a new rubber seal installed as necessary.

Automatic control of all of the components of the refrigerant recovery system 10 is carried out by an electronic controller 108 which is formed of a microprocessor having a memory storage capability and which is micro-programmable to control the operation of all of the solenoid valves SV1 through SV7 as well as the compressor motor and the condenser fan motor. Inputs to the controller 108 include a number of measured or sensed system control parameters. These control parameters may include the temperature of the storage cylinder Tstor which comprises a temperature transducer capable of accurately providing a signal indicative of the temperature of the refrigerant in the storage cylinder 86. Ambient temperature is measured by a temperature transducer positioned at the inlet to the condenser coil or condenser fan 62 and is referred to as Tamb. The temperature of the refrigerant flowing through the compressor discharge line 50 is sensed by a temperature transducer 110 positioned on the compressor discharge line 50.

Of great importance in the control scheme of the system is the compressor suction pressure designated as P2 and the compressor discharge pressure designated as P3. As indicated in FIG. 1 a pressure transducer labeled P2 is in fluid flow communication with the suction line 40 to the compressor while a second pressure transducer P3 is in fluid communication with the high pressure refrigerant line 56 passing to the condenser. The pressure ratio across the compressor 44 is defined as the ratio P3/P2. An additional input to the controller 108 is the signal from the liquid level indicator 92.

Looking now at FIG. 7 it will be noted that the operating modes of the system are identified and the condition of the electrically actuatable components of the system are shown in the different modes. In the Standby mode the system has been turned on and all electrically actuatable mechanical systems are de-energized and ready for operation. In the Service mode, the electrically actuated solenoid valves SV1 through SV4 and SV7 are all open thereby equalizing the pressures within the system so that it may be serviced without fear of encountering high pressure refrigerant.

The liquid recovery mode will now be described in detail in connection with the flow chart of FIG. 2A. It should be appreciated that the liquid recovery mode is designed to be used in larger systems for example systems having a refrigerant charge of greater than 5 pounds of refrigerant. In systems where less than 5 pounds of refrigerant are contained in the system the liquid recover mode of operation may be omitted and the operator may go directly to the vapor recover cycle which will be subsequently described.

At this point it is assumed that a system containing greater than 5 pounds of refrigerant is being serviced and that the device 10 has been coupled to the system 12 for removal of refrigerant therefrom. With reference now to FIG. 2A and FIG. 7 it will be seen that upon initiation of the Liquid Recover mode the controller 108 will open valves SV1, and SV7. The valves SV2, SV3, SV4, SV5 and SV6 will remain closed. Valves SV5 and SV6 as noted in FIG. 7 operate together as a single output from the microprocessor (controller 108) and the only time these valves are open is when the contaminant testing process is being carried out. These valves will not be discussed further in connection with other modes of operation of the system. The motors of the compressor 44 and the condenser fan 62 are also energized upon initiating the liquid recover mode.

Looking now at operation of the system in the liquid recover mode, and referring to FIG. 1. With valve SV3 closed and valve SV7 open refrigerant from the system being serviced 12 is forced by the pressure of the refrigerant in the system through conduit 20, through the T-11, through valve SV7 and via liquid refrigerant line 15 to the valve 90 on the refrigerant storage cylinder 86 and directly into refrigerant storage cylinder.

Upon entering the storage cylinder 86 at ambient conditions, a portion of the liquid refrigerant will exist in gaseous form. At this time because, the solenoid valve SV1 is open, a fluid path is directly established between the vapor outlet 88 of the storage cylinder 86 and the conduit 94 which is in communication with the low pressure side of the compressor 44. With the solenoid valve SV4 closed refrigerant passing from the condenser 60 will pass through the refrigerant expansion device 74.

Accordingly, with the control solenoids set as described above, during liquid recovery, the compressor 44 acts to withdraw low pressure gaseous refrigerant directly from the storage cylinder 86. This refrigerant passes via conduit 94 and T-96, through the T-17, and conduit 30 to the oil separator 32. From the oil separator it passes via conduit 36 to the filter drier 38, and thence via conduit 40 and accumulator 46 to the compressor 44 which delivers high pressure gaseous refrigerant via conduit 50 to the oil separator 52. From the oil separator 52 the high pressure gaseous refrigerant passes via conduit 56 to the condenser coil 60 where the hot compressed gas condenses to a liquid.

Liquified refrigerant leaves the condensing coil 60, via conduit 66 and passes through the T-connection 68 through the strainer 76 and, via conduit 72 to the refrigerant expansion device 74. The thus condensed refrigerant, at a high pressure, flows through the expansion device 74 where the refrigerant undergoes a pressure drop, and is at least partially flashed to a vapor. The liquid-vapor mixture then flows via conduit 80 and 82 back to the refrigerant storage cylinder 86 where it evaporates and absorbs heat from the refrigerant within the cylinder 86 thereby lowering the pressure and temperature within the storage cylinder 86. As a result of the lowered temperature and pressure within the storage cylinder 86 the pressure differential between the refrigeration system being serviced 12, which is at ambient temperature, and the storage tank 86 is substantially increased and, as a result the flow of liquid refrigerant through the liquid refrigerant line 15 to the storage cylinder is substantially increased.

It will be appreciated, that during this mode of operation refrigerant will continue to recirculate through the cooling and purifying circuit described above.

With reference to FIG. 2A it will be seen that the liquid recovery mode is run according to the illustrated embodiment, for two minutes at which time the system is shifted to the Cylinder Cool cycle. With reference to FIG. 7, the only difference between the operation of the system in the Cylinder Cool cycle and the liquid recovery cycle is that the solenoid value SV7 is closed and the system operates in a closed circuit, as described with no connection to the system being serviced. As the Cylinder Cool mode of operation continues the cylinder temperature continues to drop as the refrigerant is continuously circulated through the closed refrigeration circuit. Also during this time the refrigerant is passed through the refrigeration purifying components, i.e. the oil separator 32 and the filter dryer 38, a plurality of times to thereby further purify the refrigerant. The system is run in the Cylinder Cool cycle for five minutes in order to assure that the temperature and pressure within the storage cylinder is reduced such that it is substantially lower than ambient temperature.

At this point, with continued reference to FIG. 2A the system returns to the liquid recovery mode of operation. As the second liquid recovery cycle continues, the controller 108 continues to receive signals related to a number of conditions within the system. Specifically the temperature transducer Tstor provides a signal indicative of the temperature of the refrigerant in the storage cylinder 86. The pressure transducers P2 and P3, provide information with respect to the pressure entering and leaving, respectively the compressor 44. These three parameters will collectively be referred to as system control parameters.

Figure 2B:
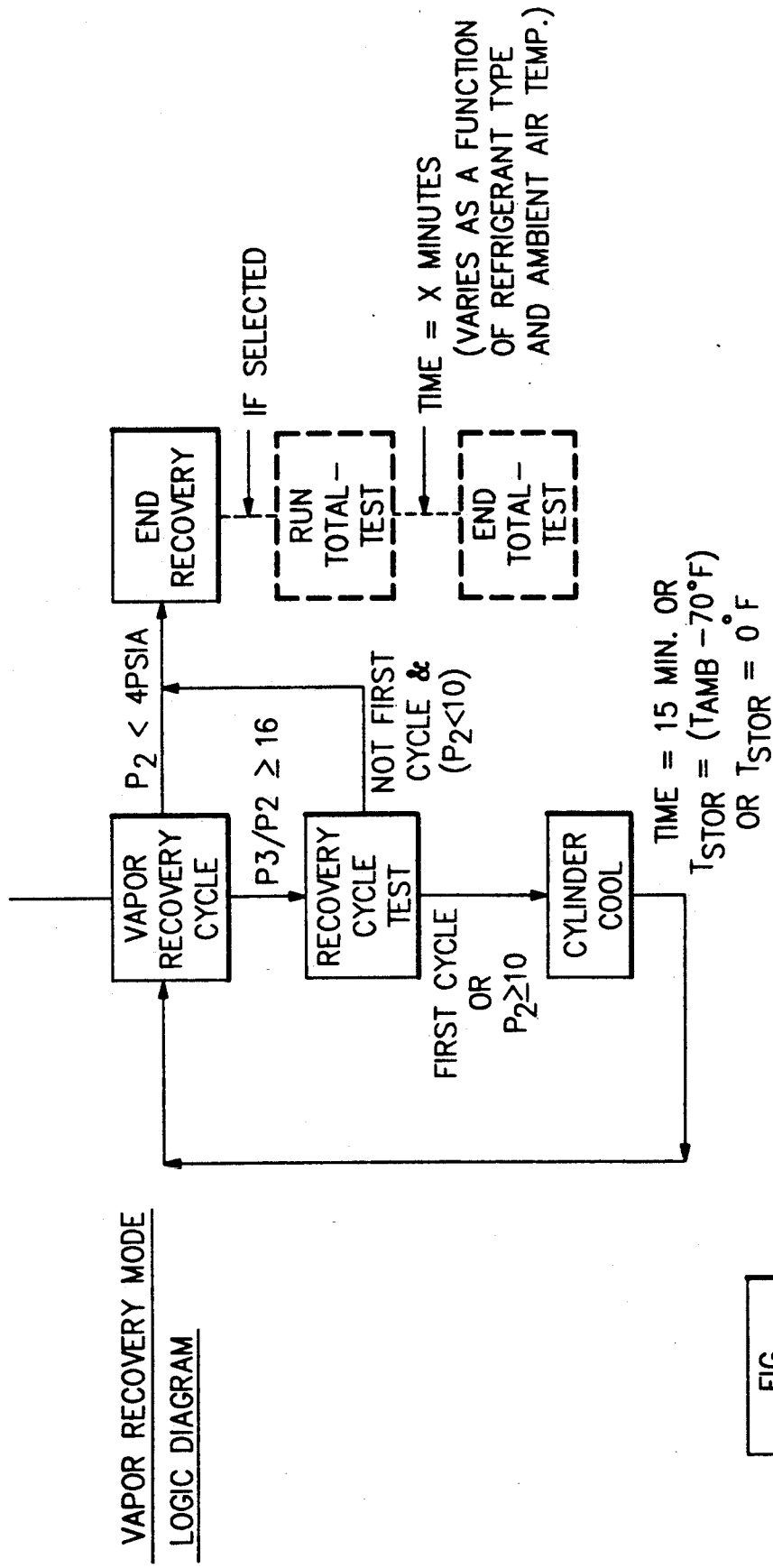
FIG. 2B is a continuation of the flow chart of FIG. 2A showing an exemplary program for controlling the system in a vapor recovery mode of operation.
Figure 3:
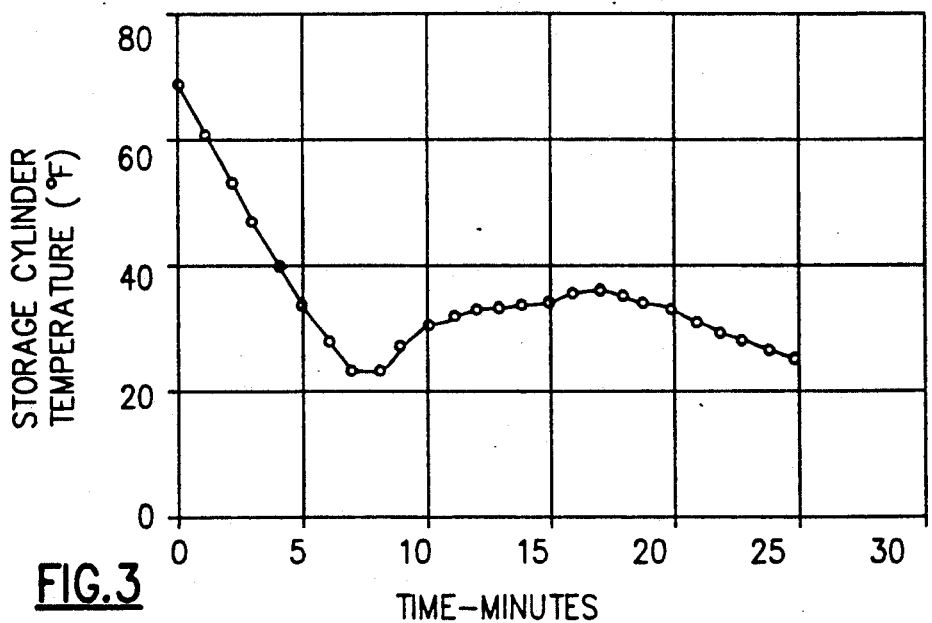
FIG. 3 is a graphical showing of storage cylinder temperature versus time in the liquid recovery mode of operation.
Figure 4:
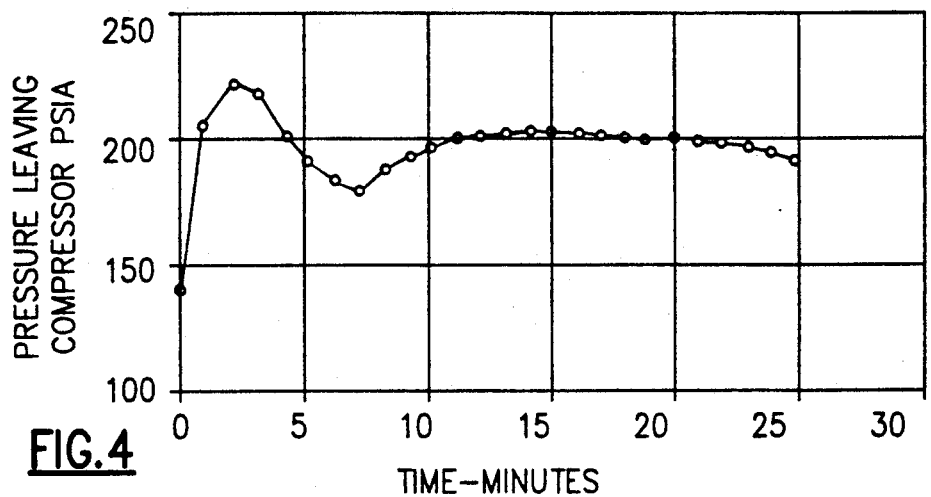
FIG. 4 is a graphical showing of pressure leaving the compressor versus time in the liquid recovery mode of operation.
Figure 5:
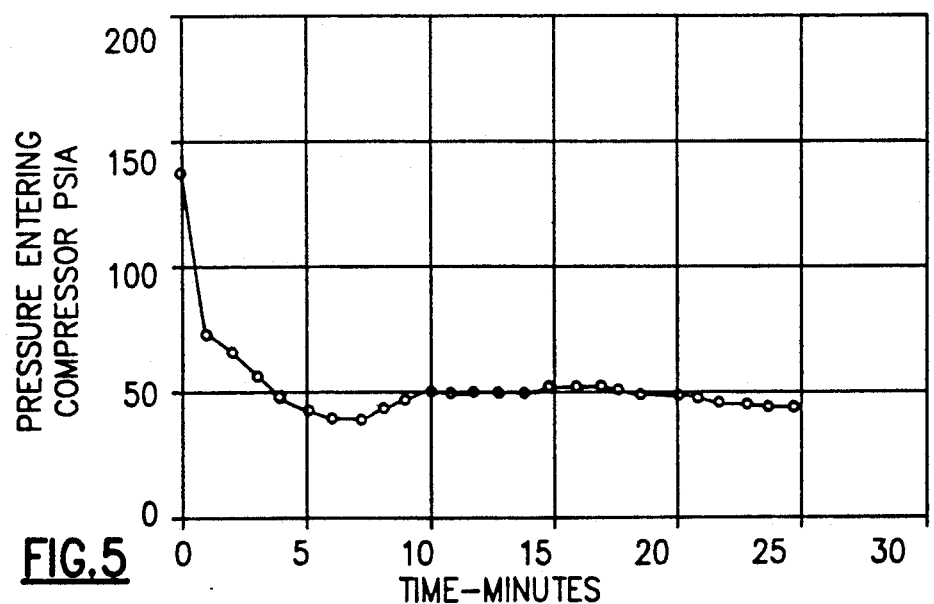
FIG. 5 is a graphical showing of pressure entering the compressor versus time in the liquid mode of operation.

FIGS. 3, 4 and 5 illustrate the value of the system control parameters Tstor, P3 and P2 respectively as a function of the length of time the liquid recovery cycle has been run. With respect to each of these graphical representations it will be noted that at the seven minute mark each of the parameters increases, then stabilizes and then begins to drop. The beginning of the increase of each of the parameters, i.e. the seven minute point represents the beginning of the second liquid recovery cycle. The point at which each of theses parameters begins to drop has been found to be correlatable with the time at which the state of the refrigerant being withdrawn from the refrigeration system 12 changes from a liquid state to a vapor state. The microprocessor of the controller 108 is programmed to terminate the recovery mode of operation automatically when one of these selected system control parameters falls a predetermined amount below its maximum value. As noted in FIG. 2A Tstor is the preferred controlled parameter and in the illustrated embodiment the termination of liquid recovery occurs when Tstor drops 5° F. from its maximum value. In the case of the control parameter being P2 or P3 a drop of 5 psi from the maximum value has been found to cause the shift from liquid recovery to vapor recovery to occur at an appropriate time.

With reference to FIG. 2A it will be seen that at this point the system shifts to a Cylinder Cool cycle of operation in order to reduce the temperature and pressure of the storage cylinder 86 prior to the beginning of a vapor recovery cycle. With continued reference to FIG. 2A, this Cylinder Cool mode of operation will terminate when any one of three conditions occur; 1) the cylinder temperature, as measured by Tstor falls to a level 70° F. below ambient temperature (Tamb), or, 2) when the Cylinder Cool mode of operation has run for a duration of 15 minutes, or, 3) when the cylinder temperature Tstor falls to 0° F. Regardless of which of the three conditions triggers termination of the Cylinder Cool mode, the result is substantially the same, i.e., the temperature (Tstor) of the refrigerant stored in the cylinder 86 is well below ambient temperature. At this point the system will shift to a vapor recovery mode of operation to complete the withdrawal of the refrigerant from the system being serviced.

The Vapor Recovery and Cylinder Cool modes will now be described in detail in connection with the flow chart of FIG. 2B. It should be appreciated that a Vapor Recovery cycle may begin under two different sets of circumstances; 1) in the case of a system containing more than five pounds of refrigerant the Vapor Recovery cycle will follow a previously performed liquid recovery cycle of operation; and 2) in the case of a refrigeration system containing less than five pounds of refrigerant the Vapor Recovery cycle represents the initiation of the recovery sequence. As the description of the Vapor Recovery and Cylinder Cool modes proceeds, some of the description will be redundant, however, for the sake of a complete understanding of the operation of the Vapor Recovery and Cylinder Cool modes a complete description from initial hookup to a refrigeration or air conditioning system 12 will be given.

The Vapor Recovery mode is the mode in which the device 10 has been coupled to an air conditioning system 12 for removal of refrigerant therefrom in the vapor state. Upon initiation of the Recover mode the controller 108 will open valves SV3 and SV4. Valves SV1, SV2, SV5, SV6 and SV7 will remain closed. The compressor 44 and the condenser fan 62 are also actuated upon initiation of the Recovery mode.

Looking now at operation of the system in the Vapor Recovery mode, and referring to FIG. 1, with valve SV3 open refrigerant from the system being serviced 12 is forced by the pressure of the refrigerant in the system, and by the suction created by operation of the compressor 44, through conduit 20, through valve SV3, check valve 98, T-17 and conduit 30 to the accumulator/oil trap 32. Within the accumulator/oil trap the oil contained in the refrigerant being removed from the system being serviced falls to the bottom of the trap along with any liquid refrigerant withdrawn from the system. Gaseous refrigerant is drawn from the accumulator/oil trap 32 through the filter dryer 38 where moisture, acid and any particulate matter is removed therefrom, and, from there passes via conduit 40, through the suction accumulator 46 to the compressor 44.

The compressor 44 compresses the low pressure gaseous refrigerant entering the compressor into a high pressure gaseous refrigerant which is delivered via conduit 50 to the oil separator 52. The oil separated from the high pressure gaseous refrigerant in the separator 52 is the oil from the recovery compressor 44 and this oil is returned via conduit 54 to the suction line 40 of the compressor to assure lubrication of the compressor. From the oil separator 52 the high pressure gaseous refrigerant passes via conduit 56 to the condenser coil 60 where the hot compressed gas condenses to a liquid. Liquified refrigerant leaves the condensing coil 60 via conduit 66 and passes through the T68 through the open solenoid valve SV4, and passes via the liquid lines 80 and 82, to the refrigerant storage cylinder 86 through liquid inlet port 84.

While refrigerant recovery is going on the controller 108 is receiving signals from the pressure transducers P3 and P2, calculating the pressure ratio P3/P2, and, comparing the calculated ratio to a predetermined value. Compressor suction pressure P2 is also being looked at alone and being compared to a predetermined Recovery Termination Suction Pressure. As shown in FIG. 2, the predetermined Recovery Termination Suction Pressure is 4 psia, and if P2 falls below this value the Recover mode is terminated and the controller 108 initiates the refrigerant quality test cycle, identified as Totaltest. This cycle will be described below following a complete description of the other modes of operation. TOTALTEST is a registered Trademark of Carrier Corporation for "Testers For Contaminants in A Refrigerant".

The selection of the predetermined recovery termination suction pressure of 4 psia results from recovery system operation wherein it has been shown that a compressor suction pressure, P2, of 4 psia or less results in recovery of 98 to 99% of the refrigerant from the system being serviced. Achieving this pressure during the first Recover mode cycle is unusual, however, it is achievable. As an example, P2 may be drawn down to the 4 psia termination value in low ambient temperature conditions where the condensing coil temperature (which is ambient air cooled) is low enough to allow P3 to remain low enough for P2 to reach 4 psia before the pressure ratio limit is reached.

Figure 2:
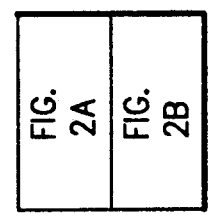
FIG. 2 is a diagram showing how FIGS. 2A and 2B fit together.

Returning now to compressor pressure ratio, as indicated in FIG. 2B, in the illustrated embodiment, when the pressure ratio exceeds or is equal to 16 the microprocessor in the controller 108 performs what is referred to as the Recovery Cycle Test. If the Recovery Cycle just performed is the first Recovery Cycle performed and the compressor suction pressure P2 is greater than or equal to 10 psia the system will shift to what is known as a Cylinder Cool mode of operation. If the Recovery Cycle just performed is a second or subsequent recovery cycle and the compressor suction pressure P2 is less than 10 psia the controller will consider the refrigerant Recovery as completed and will initiate the refrigerant contaminant test cycle (Totaltest).

The latter conditions, i.e. second or subsequent recover cycle, and P2 less than 10 psia, are conditions that are found to exist at high ambient temperatures. For example, such conditions may exist when recovering R-22 from an air conditioning system at an ambient temperature of 105° F. and above. Under such conditions it has been found that attempts to reduce the compressor suction pressure P2 to values less than 10 psia are counterproductive in that a substantial length of operating time would be necessary in order to obtain a very small additional drop in suction pressure. Further, it has been found, at these conditions, that shifting to the Cylinder Cool mode, which will be described below, also would not substantially increase the amount of refrigerant that would ultimately be withdrawn from the system and accordingly termination of the Vapor Recovery mode and initiation of the refrigerant contaminant test cycle is indicated.

Assuming that the Recovery Cycle Test has indicated that either: it is the first recovery cycle, or, the compressor suction pressure P2 is greater than or equal to 10 psia, the controller 108 will initiate the Cylinder Cool mode of operation.

In the Cylinder Cool mode, as indicated in FIG. 7, solenoid valve SV1 is energized and thereby in the open condition. Solenoid valves SV2, SV3 and SV4 are closed, and, the compressor motor and condenser fan motor continue to be energized. The Cylinder Cool mode of operation essentially converts the system to a closed cycle refrigeration system wherein the refrigerant storage cylinder 86 functions as a flooded evaporator. By closing solenoid valve SV3 the refrigerant recovery and purification system 10 is isolated from the refrigeration system 12 being serviced. The opening of solenoid valve SV1 establishes a fluid path between the vapor outlet 88 of the storage cylinder 86 and the conduit 28 which is in communication with the low pressure side of the compressor 44. The closing of solenoid valve SV4 routes the refrigerant passing from the condenser 60 through the refrigerant expansion device 74.

With the control solenoids set as described above, in the Cylinder Cooling mode of operation the compressor 44 compresses low pressure gaseous refrigerant entering the compressor and delivers a high pressure gaseous refrigerant via conduit 50 to the oil separator 52. From the oil separator 52 the high pressure gaseous refrigerant passes via conduit 56 to the condenser coil 60 where the hot compressed gas condenses to a liquid. Liquified refrigerant leaves the condensing coil 60 via conduit 66 and passes through the T-connection 68 through the strainer 76 and, via conduit 72, to the refrigerant expansion device 74. The thus condensed refrigerant, at a high pressure, flows through the expansion device 74 where the refrigerant undergoes a pressure drop, and is at least partially, flashed to a vapor. The liquid-vapor mixture then flows via conduits 78 and 82 to the refrigerant storage cylinder 86 where it evaporates and absorbs heat from the refrigerant within the cylinder 86 thereby cooling the refrigerant.

Low pressure refrigerant vapor then passes from the storage cylinder 86, via vapor outlet port 88, through conduit 94 and solenoid valve SV1 to the T connection 96. From there it passes through the check valve 98, T-17, conduit 30, the oil separator/accumulator 32, filter dryer 38 and conduit 40 to return to the compressor 44, to complete the circuit.

As the Cylinder Cool mode of operation continues, the cylinder temperature, as measured by the temperature transducer Tstor, continues to drop as the refrigerant is continuously circulated through the closed refrigeration circuit. Also during this time the refrigerant is passed through the refrigeration purifying components, i.e. the oil separator 32 and the filter dryer 38, a plurality of times to thereby further purify the refrigerant.

Referring again to FIG. 2, the Cylinder Cool mode of operation will terminate when any one of three conditions occur; 1) the cylinder temperature, as measured by Tstor falls to a level 70° F. below ambient temperature (Tamb), or, 2) when the Cylinder Cooling mode of operation has gone on for a duration of 15 minutes, or, 3) when the cylinder temperature Tstor falls to 0° F. Regardless of which of the three conditions has triggered the termination of the Cylinder Cool mode the result is substantially the same, i.e., the temperature (Tstor) of the refrigerant stored in the cylinder 86 is now well below ambient temperature. As a result, the pressure within the cylinder, corresponding to the lowered temperature is substantially lower than any other point in the system.

When any one of the Cylinder Cool mode termination events occur, the controller 108 will shift the system to a second Recover mode of operation. In the second Recover mode the solenoid valves, and compressor and condenser motors are energized as described above in connection with the first Recover mode. Because of the low temperature Tstor that has been created in the refrigerant storage cylinder, however, the capability of the system to withdraw refrigerant from the unit being serviced, without subjecting the recovery compressor to high pressure differentials is dramatically increased.

An understanding of this phenomenon will be appreciated with reference to FIG. 1. It will be described by picking up a Recover cycle at the point where refrigerant withdrawn from the system being serviced is discharged from the compressor 44 and is passing, via conduit 56, to the condenser 60. At this point the pressure within the system, extending from the compressor discharge port 48 through to and including the storage cylinder 86, is dictated by temperature and pressure conditions within the storage cylinder 86. As a result the storage cylinder 86 now effectively serves as a condenser with the recovered refrigerant passing as a super-heated vapor through the condenser coil, through the solenoid valve SV4 and the conduits 80 and 82 to the storage cylinder 86 where it is condensed to liquid form.

It is the dramatically lower compressor discharge pressure P3 experienced during a second or subsequent Recover mode (i.e. any Recover mode following a Cylinder Cool mode) that allows the recovery compressor 44 to draw the system being serviced 12 to a pressure lower than heretofore obtainable while still maintaining a permissible pressure ratio across the recovery compressor.

It will be appreciated that in a second Recover mode, the pressure ratio P3/P2 could exceed the predetermined value (which in the example given is 16) and, depending upon the other system conditions, as outlined in the flow chart of FIG. 2, will result in an additional Cylinder Cool mode of operation or termination.

With continued reference to FIG. 2B, the system will operate as described until conditions exist which result in the controller 108 switching to the refrigerant purity test (Totaltest) mode of operation. This mode of operation will now be described in detail in connection with a refrigerant recovery and purification system, it should be appreciated however that it may be desirable to have a refrigerant purity test circuit installed in many refrigeration systems in order to facilitate making a check of the purity of the refrigerant flowing through the system while it is in operation and, without venting any refrigerant to the atmosphere. Accordingly, the refrigerant purity test system described herein may be readily adapted to virtually any refrigeration system having a compressor.

Figure 8:
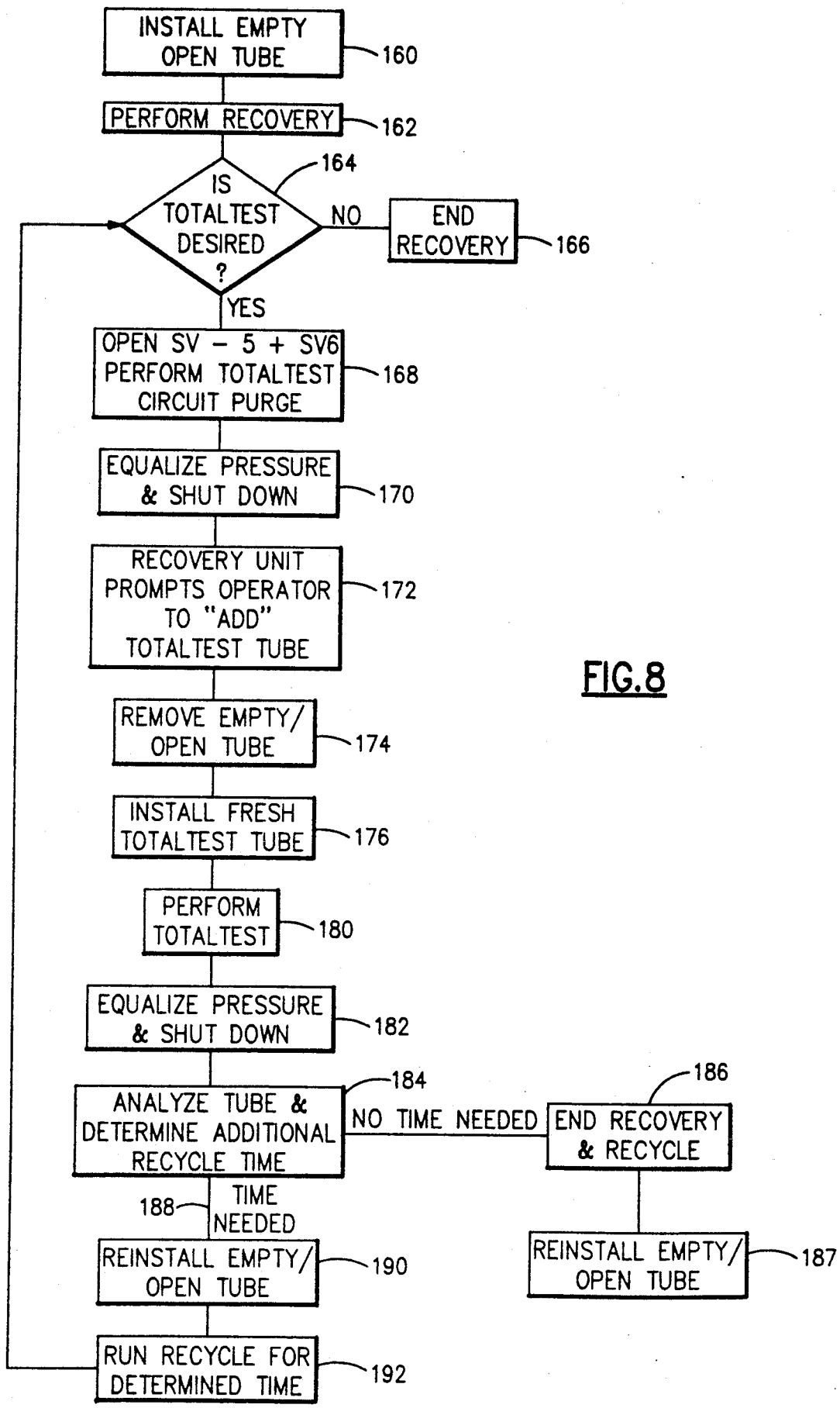
FIG. 8 is a flow diagram showing the steps involved in the refrigerant purity testing method of the present invention.

Referring now to FIG. 8 a flow chart showing the sequence of steps taken in performing the refrigerant purity test is shown. The refrigerant purity test feature automatically samples refrigerant for acid and moisture contamination. The refrigerant purity test may be used after a recovery cycle or a recycle mode of operation.

The FIG. 8 flow chart describes the system in connection with performance of a typical refrigerant recovery operation. Step 160 requires that the operator install, in the sampling tube holder 110, an empty "dummy" refrigerant purity test tube that contains no chemicals and which is open at both ends. The "dummy" tube may be made of glass, plastic or metal, and, in appearance will be substantially identical to the tube 140 shown in FIGS. 9 and 10. This tube, preferably, remains in the test fixture at all times except when a purity test is being performed, as will be described hereinafter. Step 162 indicates the performance of a recovery cycle by the recovery and purification system 10 and when that cycle is completed as discussed in detail hereinabove, the microprocessor 108 looks to its inputs to see if a refrigerant purity test has been selected as indicated in step 164. If it has not, the recovery ends as indicated at 166 and the system shuts down. If a refrigerant purity test has been selected the system will shut down to allow installation of a fresh active refrigerant purity test tube. Prior to shut down the system will perform a purge cycle as indicated by step 168. During the purge cycle, the solenoid valves SV6 and SV5 at the entrance and exit, respectively, of the sampling tube holder 110 are opened for 15 seconds and refrigerant flows through the refrigerant purity test circuit, including the dummy tube, to purge the refrigerant purity test circuit piping and fixture of any residual moisture or contaminated refrigerant. At the end of the purge cycle the microprocessor equalizes the pressure within the system and shuts down as shown in step 170. This is a accomplished by shutting off the compressor and opening solenoid actuated valves SV1, SV2, and SV4.

Following equalization all of the solenoid actuated valves SV1 through SV7 are turned off and the microprocessor controller 108 prompts the operator by way of a visual display on the units console 111 showing the word "ADD" as indicated at 172. This prompt directs the user to remove the "dummy" tube from the sampling tube holder 110 and to install an active refrigerant purity test tube into the fixture as indicated at step 174 and 176. When this is done the operator is instructed to push the units "start" button 178 (also on the console). When this is done the unit 10 restarts and a "Totaltest" refrigerant purity sample is taken. The refrigerant purity test 180 actually includes two steps. The first being operation of the system in a pre-purity test mode for 30 seconds to assure that the refrigerant contained within the units piping and components is representative of that contained in the storage cylinder 86. Upon initiation of the pre-purity test mode of operation, solenoid valves SV1, SV2, and SV4 are all energized to an open position. The solenoid valves SV3, SV5/SV6 and SV7 are not energized and are therefore closed. With the flow control valves in the condition described the flow of refrigerant through the recovery system is similar to that described above in connection with the Cylinder Cooling mode with two important exceptions, first the solenoid valve SV4 is open and therefore the refrigerant does not pass through the expansion device 74. The second important exception is that with SV2 open the refrigerant drawn from the storage cylinder via conduit 94 will be drawn through the refrigerant sampling conduit 29 and into the compressor suction line 40. At this time the refrigerant sampling conduit 29 and the purification components 32 and 38 are in parallel fluid flow relationship. Because the pressure drop through the purification components, is substantially greater, most of the flow will be through conduit 29. As a result, under these conditions, the refrigerant circulating in the system is of the same purity as the refrigerant contained in the storage cylinder 86.

Following the 15 second pre-purity test mode, the solenoid valves SV5 and SV6 are opened and a flow of refrigerant representative of that contained within the storage cylinder 86 passes through the refrigerant quality test tube. The flow of refrigerant through the refrigerant quality test tube is caused by the pressure differential existing between the high and low pressure sides of the system which induces the flow of refrigerant through conduit 102, solenoid valve SV6, the sampling tube holder 110 (and the tube contained therein), solenoid valve SV5 and conduits 106 and 23 to thereby return the refrigerant being tested to the suction side of the compressor 44. A suitable orifice is provided in conduit 104, to provide the necessary pressure drop to assure that the flow of refrigerant through the testing tube held in the sampling tube holder 104 is at a rate that will assure that the testing tube will receive the proper flow of refrigerant therethrough during the TOTALTEST run time in order to assure a reliable test of the quality of the refrigerant passing therethrough. After a specified period of time, dependent upon the type of refrigerant being tested and other variables all of which is programmed into the controllers microprocessor, the system then equalizes its pressure and shuts down as indicated by step 182 in the same manner as described hereinabove with respect to step 170.

Following this shut down, as indicated in step 184 the user is instructed to immediately determine the length of chemical discoloration or staining on the refrigerant purity test tube and to ascertain from the materials supplied by the test tube manufacturer the refrigerant acid and moisture level within the refrigerant. This analysis should be done before removing the purity test tube from the fixture. If the analysis of the tube indicates that the acid and moisture levels are within acceptable limits the recovery and recycle procedure is ended as indicated by step 186. The use should the remove the used purity sample tube and reinstall the "dummy" tube as indicated at step 187. If the analysis indicates that additional recycle time is needed path 188 is followed and the user is also instructed to remove the used purity sample tube and reinstall the "dummy" tube as indicated at step 190.

Following installation of the "dummy tube the recovery and purification unit 10 is then activated to run for an additional recycle, i.e. purification, mode for the desired time. Following this recycle, 192 the system returns to the step 164 where the question is again asked whether a refrigerant purity test is desired and the system runs through the described cycle until the system is shut down either via step 166 or step 186. At this time all of the refrigerant contained within the cylinder 86 has been dried and purified to the derived degree and ready for reuse.

Figure 6:
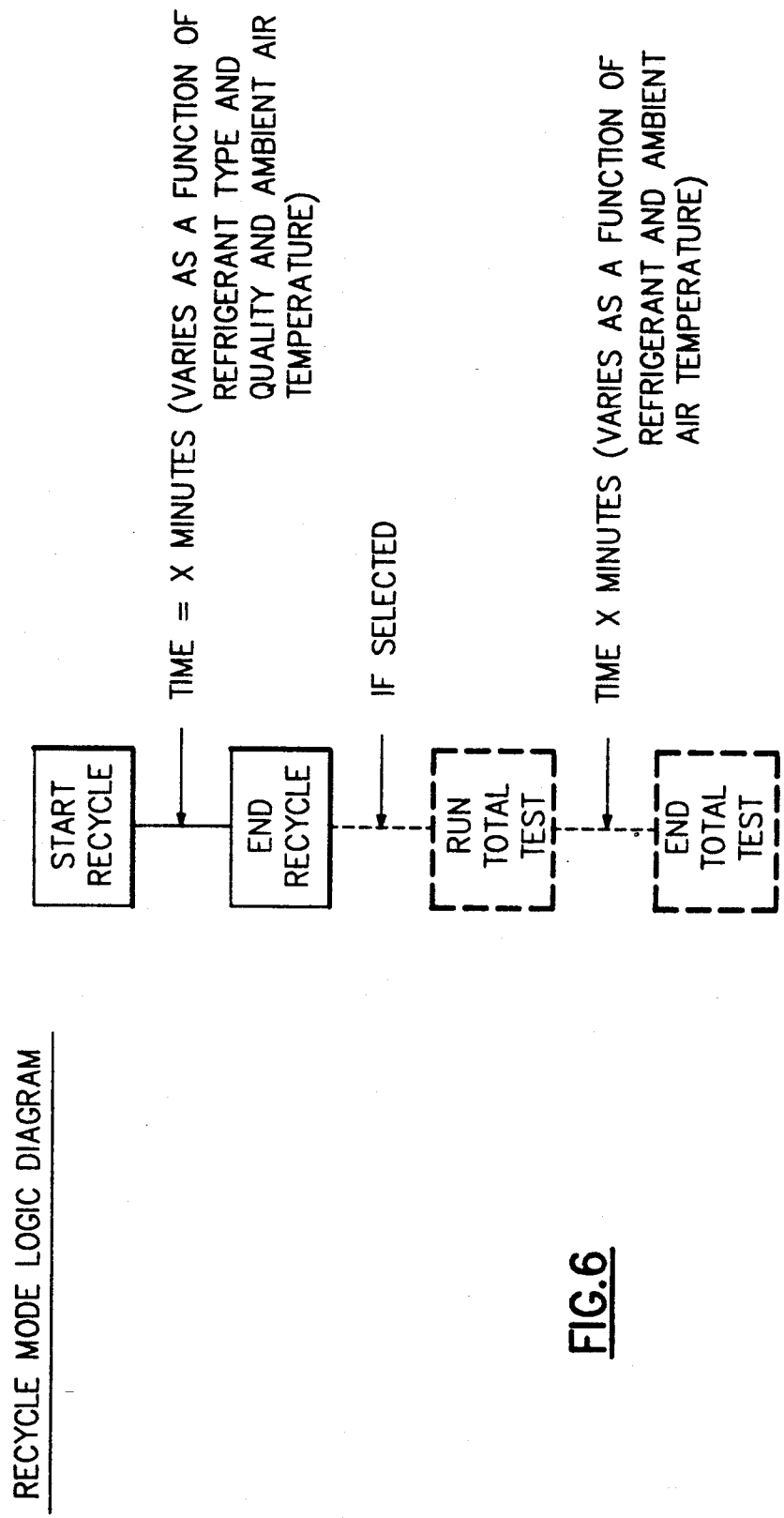
FIG. 6 is a flow chart of an exemplary program for controlling the system in a recycle mode of operation.

With reference to FIG. 6 the length of time in which the system is run in the Recycle mode is determined by the operator as a number of minutes "X" which varies as a function of refrigerant type and purity and ambient air temperature. The type of refrigerant is known, the ambient temperature may be measured, and the purity is determined by the operator upon the evaluation of the test tube used in the refrigerant purity test cycle. With continued referenced to FIG. 6, upon the end of the selected recycle time the system, if so selected by the operator, will run another refrigerant purity test, and, if the results of this test so indicate another recycle period may be initiated following the procedure set forth above.

The object of the system and control scheme described above is to remove as much refrigerant as possible from a system being serviced, under any given ambient conditions, or system conditions, while, at all times monitoring system control parameters which will assure that the compressor of the Recovery system is not subjected to adverse operating conditions. As described above, the system control parameter is the pressure ratio $P_3/P_2$, across the recovery compressor 44. In the example given above a value of $P_3/P_2$ of 16 was used as the pressure ratio above which the compressor could be adversely affected. It should be appreciated that for different compressors the value of this parameter could be different.

The ultimate goal in the control of this system is to limit compressor operation to predetermined limits to assure long and reliable compressor life. As pointed out above, in the Background of the Invention. the internal compressor temperature is considered by compressor experts to be the controlling factor in preventing internal compressor damage during operation. In the presently disclosed embodiment the pressure ratio has been found to be an extremely reliable effective control parameter which may be related to the internal compressor temperature and has thus been selected as the preferred control parameter in the above described preferred embodiment. Pressure differential, (i.e. $P_3-P_2$) could also be effectively used to control the system.

It should be appreciated however, that other system control parameters such as the compressor discharge temperature as measured by the temperature transducer 110 in the compressor discharge line 50, or the compressor suction pressure $P_2$ could also be used to control the operation of the system, to limit the system to operation only at conditions at which the compressor is not adversely effected.

With respect to temperature, it is generally agreed that an internal compressor temperature at which the lubricating oil begins to break down is about 325° F. Above this temperature adverse compressor operation and damage may be expected. In the present system the controller 108 has been programmed such that, should the compressor discharge temperature, monitored by the temperature transducer 110 exceed a maximum of 225° F. regardless of pressure ratio conditions, the system will be shut off.

It is further contemplated that, if the compressor discharge temperature, as measured at the transducer 110 were used as the primary system control parameter that a temperature in the neighborhood of 200° F. would be used to switch the recovery system from a Recover mode to a Cylinder Cooling mode of operation in order to assure that the compressor would not be adversely affected during operation of the system.

According to another control method, as mentioned above, the system control parameter being sensed for compressor protection could be the compressor suction pressure P2. In this case the microprocessor of the controller 108 would be programmed with compressor suction pressures P2 which would be considered indicative of adverse compressor operation, for a range of ambient air temperatures and for the different refrigerants which may be processed by the system. As an example, when processing refrigerant R-22 at an ambient air temperature of 90° F. a suction pressure P2 in the range of 13 psia to 15 psia would be programmed to change the system from a Recover mode Cylinder Cooling mode of operation.

The outstanding refrigerant recovery capability of a system according to the present invention is reflected in the following example. The recovery apparatus was connected to a refrigeration system having a system charge of 40.0 pounds of refrigerant R-22 at an ambient temperature of 70° F. Such a system is typical of a large central air condition system.

Upon initiation of liquid recovery the system performed the liquid recovery sequence for a duration of 15 minutes before shifting to the vapor recovery mode of operation. At the point of initiation of vapor recovery 37.7 pounds had been recovered from the system. Vapor recovery was then initiated and ran for 10 minutes during which time an additional 2.1 pounds of refrigerant was recovered. At this point, the total run time had been 25 minutes and a total of 39.8 pounds of refrigerant had been recovered from the system. This represents 99.5% of the total charge of 40.0 pounds, leaving only 0.2 pounds in the system.

The outstanding refrigerant recovery capability of a system according to the present invention is further reflected in the following example of vapor recovery only. The recovery apparatus was connected to a refrigeration system having a system charge of 4.5 pounds of refrigerant R-12 at an ambient temperature of 70° F. Such a system is typical of an automobile air conditioning system.

Upon initiation of recovery the system performed a first Recover cycle for 8.67 minutes before the system reached the limiting pressure ratio $P_2/P_3$ of 16. At that point 3.73 pounds had been recovered from the system. This represents 82.9% of the systems total charge. Typical prior art systems would stop at this point, leaving 0.77 pounds, or more than 17% of the charge in the system. This 0.77 pounds would eventually be released to the atmosphere.

At this point, the system shifted to the Cylinder Cool mode of operation. The Cylinder Cool cycle ran for 15 minutes, bringing the cylinder temperature (Tstor) down to 10° F. At this point a second Recover cycle was initiated by the system controller. The second Recover cycle ran for 3.8 minutes at which time Recover was terminated when the suction pressure P2 fell to 4.0 psia.

At this point, the total system run time had been 27.5 minutes and a total of 4.42 pounds of refrigerant had been recovered from the system. This represents 98.2% of the total charge of 4.5 pounds, leaving only 0.08 pounds in the system.

Following completion of recovery and purification, the storage cylinder 86 contains clean refrigerant which may be returned to the refrigeration system. With reference to FIG. 4, the Recharge mode, when selected, results in simultaneous opening of valves SV1 and SV3 to establish a direct refrigerant path from the storage cylinder 86 to the refrigeration system 12. All other valves and the compressor and condenser are de-energized in this mode. The amount of refrigerant to be delivered to the system is selected by the operator, and, the controller 108, with input from the liquid level sensor 92 will assure accurate recharge of the selected quantity of refrigerant to the system.

This invention may be practiced or embodied in still other ways without departing from the spirit or central character thereof. The preferred embodiments described herein are therefore illustrative and not restricted. The scope of the invention being indicated by the appended claims and all variations which come within the meaning of the claims are intended to be embraced therein.

What is claimed:

1. A method of testing the purity of refrigerant flowing through a refrigeration system the refrigeration system having a normal non-testing mode of operation, the refrigeration system including, a compressor having an inlet port which has an inlet conduit associated therewith defining in part the low pressure side of the refrigeration system, an outlet port having an outlet conduit associated therewith defining in part the high pressure side of the refrigeration system, a refrigerant purity testing system including, a refrigerant purity testing holder for removably supporting a refrigerant purity testing tube in fluid flow relationship therewith, a first conduit for establishing fluid communication between one end of the tube holder and with the inlet conduit, and a second conduit for establishing fluid communication between the other end of the tube holder and the outlet conduit, the first and second conduits each having a flow control valve which may be open or closed, the method comprising;

a) installing an empty open ended testing tube in the tube holder;
 b) closing the flow control valves in the first and second conduits;
 c) starting the compressor;
 d) operating the refrigeration system in a normal mode;
 e) opening the flow control valves in the first and second conduits when it is desired to test the purity of the refrigerant in the refrigeration system;
 f) operating the refrigeration system for a predetermined period of time with the flow control valves open, to thereby purge the refrigerant purity testing system;

g) closing the flow control valves in the first and second conduits after said predetermined time;

h) shutting off the compressor;

i) operating the refrigeration system in a pressure equalization mode for a predetermined period of time;

j) removing the empty open ended testing tube from the tube holder;

k) installing a fresh refrigerant purity testing tube in the tube holder;

l) starting the compressor;

m) opening the flow control valves in the first and second conduits;

n) operating the refrigeration system in a refrigerant purity sampling mode for a predetermined period of time; and o) analyzing the refrigerant purity test tube after the predetermined period of time to determine the purity of the refrigerant in the refrigeration system.

2. The method of claim 1 wherein the refrigeration system includes means for purifying refrigerant, and, wherein the step of analyzing the refrigerant purity test indicates that the purity of the refrigerant is not acceptable, further comprising the steps of;

closing the flow control valves in the first and second conduits;

shutting off the compressor;

operating the refrigeration system in a pressure equalization mode;

removing the now used refrigerant purity test tube installed in step K;

reinstalling the empty open-ended testing tube in the tube holder;

starting the compressor; and operating the refrigeration system in a purification mode.

3. The method of claim 1 including performing the following step in between steps l) and m);

operating the refrigeration system in a normal mode for a predetermined period of time before performing step m).

* * * * *